(12) United States Patent
Whitley

(10) Patent No.: US 7,993,328 B2
(45) Date of Patent: *Aug. 9, 2011

(54) SELF-SEALING MALE LUER CONNECTOR WITH MULTIPLE SEALS

(75) Inventor: Kenneth W. Whitley, Raleigh, NC (US)

(73) Assignee: CareFusion 303, Inc., San Diego, CA (US)

( * ) Notice: Subject to any disclaimer, the term of this patent is extended or adjusted under 35 U.S.C. 154(b) by 116 days.

This patent is subject to a terminal disclaimer.

(21) Appl. No.: 12/497,496

(22) Filed: Jul. 2, 2009

(65) Prior Publication Data

US 2010/0004634 A1     Jan. 7, 2010

Related U.S. Application Data

(63) Continuation of application No. 11/009,444, filed on Dec. 10, 2004, now Pat. No. 7,645,274.

(51) Int. Cl.
*A61M 25/16* (2006.01)

(52) U.S. Cl. ...................................................... 604/537

(58) Field of Classification Search .................. 604/537, 604/538, 539, 247, 249, 256; 251/142, 149, 251/149.1

See application file for complete search history.

(56) References Cited

U.S. PATENT DOCUMENTS

| | | | |
|---|---|---|---|
| 5,738,144 A | 4/1998 | Rogers | |
| 6,344,033 B1 | 2/2002 | Jepson et al. | |
| 6,543,745 B1 | 4/2003 | Enerson | |
| 6,595,981 B2 * | 7/2003 | Huet | 604/523 |
| 6,964,406 B2 | 11/2005 | Doyle | |
| 7,044,441 B2 | 5/2006 | Doyle | |
| 7,140,592 B2 * | 11/2006 | Phillips | 251/149.6 |
| 7,306,566 B2 | 12/2007 | Raybuck | |
| 7,645,274 B2 * | 1/2010 | Whitley | 604/537 |

FOREIGN PATENT DOCUMENTS

EP     0 574 908 A1     12/1993

OTHER PUBLICATIONS

International Search Report dated Apr. 11, 2006 in related PCT application No. PCT/US2005/043973; International Filing Date Dec. 2, 2005.

* cited by examiner

*Primary Examiner* — Matthew F Desanto
(74) *Attorney, Agent, or Firm* — McDermott Will & Emery LLP

(57) ABSTRACT

A self-sealing male Luer connector attaches to any standard female Luer valve to open a flow channel between the two. The self-sealing male Luer connector includes a rigid housing having a distal end with a rigid male Luer connector and a proximal end at which a proximal seal is formed. The distal end of the housing includes a valve seat. Located within the housing is a resilient biasing member that biases an actuator into contact with the valve seat to prevent fluid flow through the male connector. Upon engagement with a female connector, the actuator is moved in the proximal direction to open the distal valve and then the proximal seal. A partial vacuum is formed within the male connector upon disengagement with the female connector that draws any fluids on the external surface of the distal end of the male Luer connector into the male tip.

14 Claims, 7 Drawing Sheets

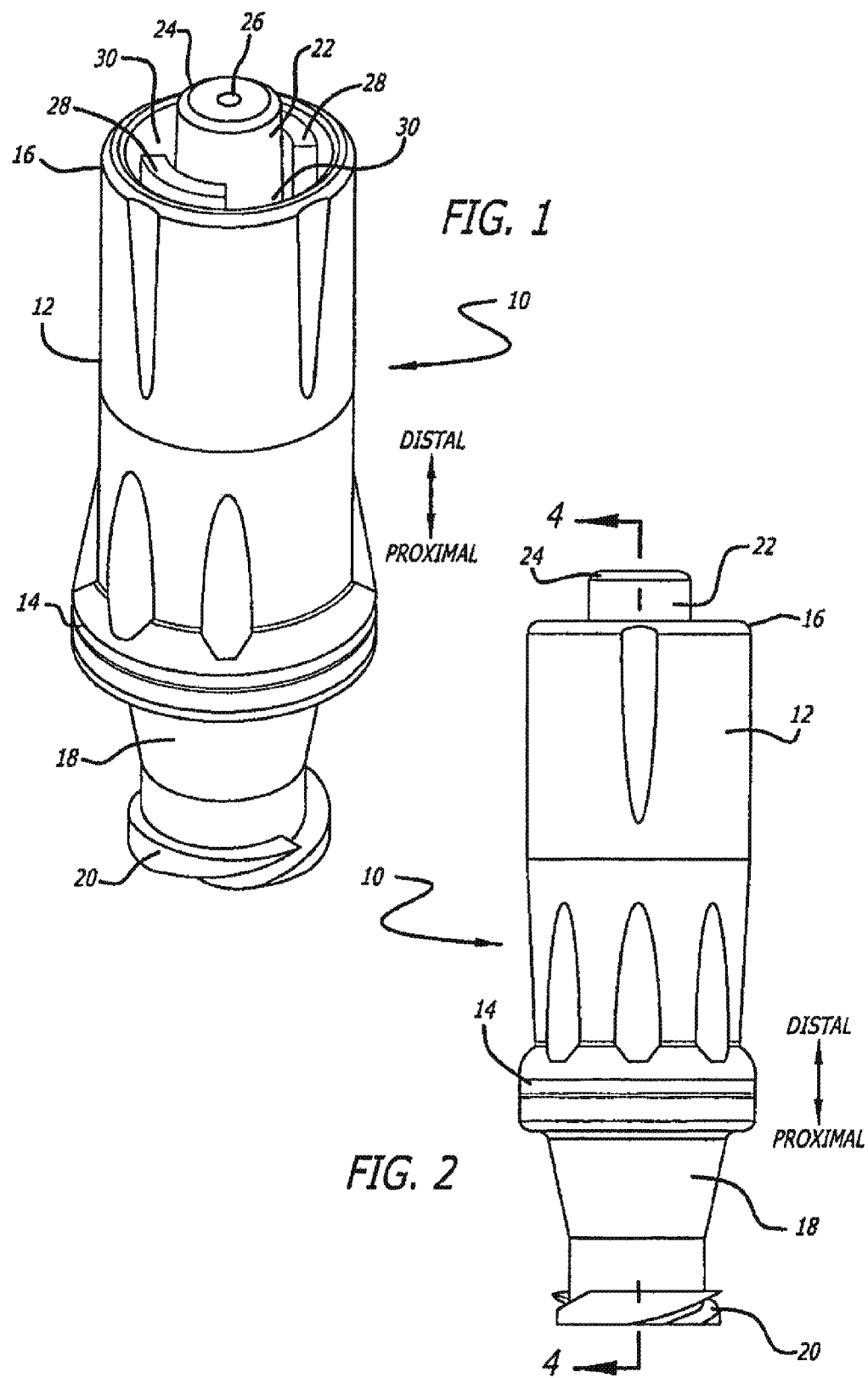

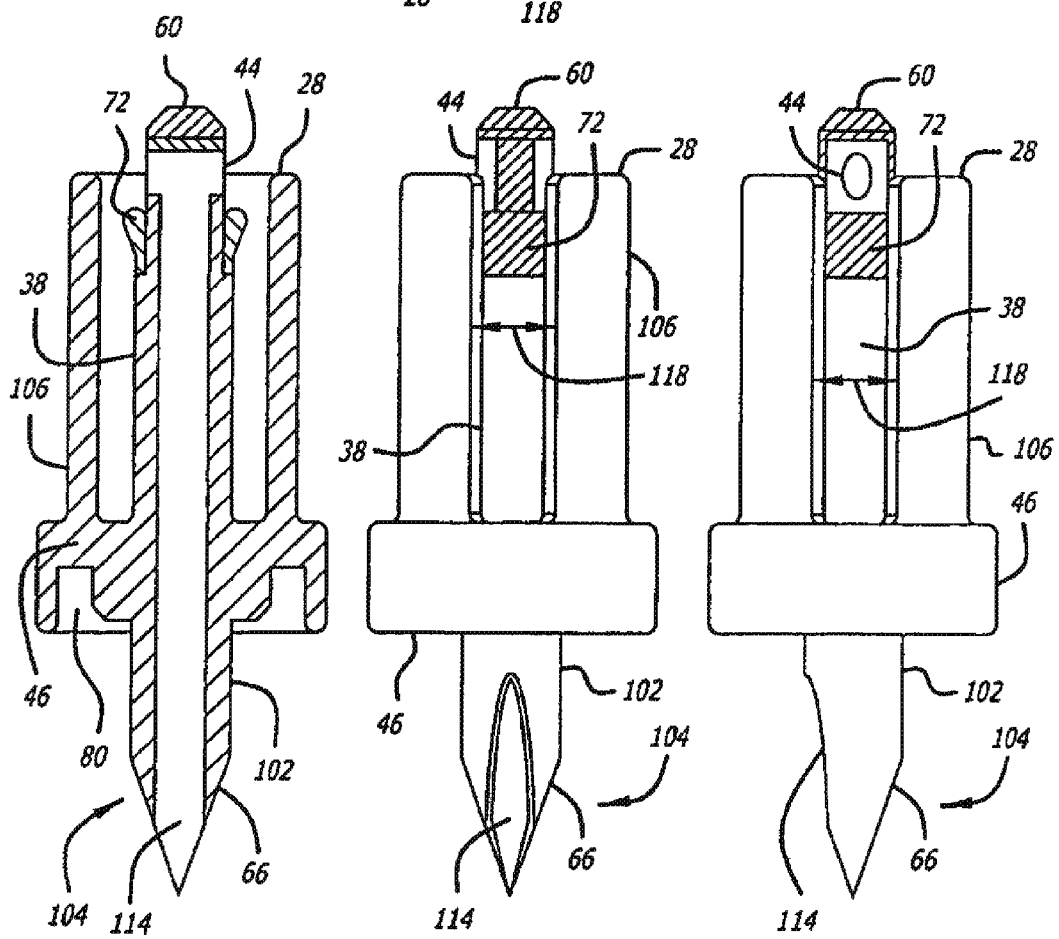

SELF-SEALING MALE LUER CONNECTOR WITH MULTIPLE SEALS

This application is a continuation of U.S. application Ser. No. 11/009,444, filed Dec. 10, 2004, now issued as U.S. Pat. No. 7,645,274, which is incorporated herein by reference in its entirety for all purposes.

BACKGROUND OF THE INVENTION

The invention relates generally to male connectors that allow for the passage of fluid once connected, and more particularly, to a self-sealing male connector having an internal valve structure that is automatically actuated to permit flow once properly connected to a female connector.

The self-sealing medical connectors presently known and used in the art are generally designed to be connected to a patient's intravenous ("I.V.") or gas sampling line, drug or solution source, or other medical device such that the connector's seal operates to trap all fluid on the side of the connector toward the patient or other device. As such, the typical connector has an unsealed male Luer connector on one end that remains connected to the patient's I.V. line, fluid source or other device and a self-sealing female connector on the opposite free end of the connector through which a syringe or other such device may be engaged. The self-sealing female connector typically has an internal valve that is opened upon connection with a male connector and which automatically closes upon disconnection from the male connector.

In use, the syringe or other device having a male connector is connected to the female end of the connector to push or pull fluids through the female connector, as when medications are dispensed within a patient's I.V. line. The syringe or other device is configured with a male connector so as to engage the self-sealing female connector and cause the male connector's central boss to contact the female connector's seal membrane, opening the internal valve of the female connector and creating a fluid path through the female connector. After the necessary fluids have been dispensed or withdrawn, the syringe is removed and the internal valve in the female needle-free connector closes to reseal the female connector and trap all bodily fluids, including any just-dispensed medications, on the patient side of the connector. However, the male connector of the syringe typically does not include an internal valve and any residual fluids remaining therein are unsealed and exposed.

In the medical industry, there are applications in which the fluid being dispensed from or drawn into the syringe or other device or container must itself be at all times sealed off and exposure of the care giver to such fluid prevented or at least minimized. For example, in the area of nuclear medicine where radioactive isotopes are administered to patients, it is critical that exposure to the isotopes be minimized for the safety of both the care giver and the patient. A further example includes collecting blood from a patient, were it is important to prevent exposure of the blood remaining in the collection device to the care giver.

Yet a further example is in the oncology area where certain drugs have great beneficial effect when confined to the circulatory system of a patient, yet are harmful to the skin or other tissues of a patient. Such drugs must be carefully controlled so that they do not reach tissues that may be harmed. Transferring such drugs from one container to another or to the patient's fluid line can be hazardous if seals are not present.

For these purposes, a different self-sealing, needle-free male Luer connector design is desirable. Where even the slightest amount of contact between such strong medical fluids and the clinician or the patient's outer tissue is to be avoided, it would be highly beneficial to provide a male connector that is able to minimize the existence of such fluids on its outer surfaces. In the case where such fluids inadvertently reside on such outer surfaces, such a connector should provide a means of removing the fluids form those surfaces.

It is becoming more and more common for connectors to use Luer shapes. This is because an international standard has been adopted for such shapes; see ISO No. 594. Such Luer shapes have a tapered outer surface for male connectors and a complementary tapered inner surface for female connectors. Such tapering permits connectors having less precise dimensions to still successfully mate for fluid transfer. For more secure connection, threads or thread elements have been added to the outer surface surrounding the female connector's opening and a threaded collar has been added about the male Luer connector. The threaded collar may freely rotate or may be fixed in position about the male Luer connector. Because of the wide availability of female connectors and female valve ports, it would be desirable to provide a self-sealing male connector having a Luer shape.

Hence, those skilled in the art have recognized a need for a self-sealing male connector to seal off residual fluids therein before and after connection to a female connector. Such a self-sealing male connector may be connected to or formed as part of a syringe or other device, or formed on a blood collection device, or may be used with tubing or other devices for controllably conducting medical fluids, including more dangerous fluids that are toxic or corrosive. An additional need has been recognized for a self-sealing male connector that also self cleans its outer surfaces. The present invention fulfills these needs and others.

SUMMARY

Briefly and in general terms, the invention is directed to a self-sealing male connector for connection with a female connector, the male connector comprising a rigid housing having a distal end and a proximal end, the housing comprising at the distal end a rigid tubular male portion having a shape configured for engagement with a female connector, a distal valve located at the distal end of the housing, the distal valve comprising an internal valve seat disposed in the tubular male portion, a proximal valve located at the proximal end of the housing, and an actuator disposed within the housing and configured to be movable towards the proximal end of the housing to cause opening of both the distal and proximal valves, the actuator comprising an actuator arm disposed adjacent and outside the tubular male portion wherein movement of the actuator arm from a first position to a second position causes towards the proximal end of the housing thereby opening both the distal and proximal valves, whereby the actuator arm is configured to move from the first position to the second position when a female connector is engaged with the tubular male portion.

In more detailed aspects, the connector further comprises a resilient member contained within the housing and positioned to bias the actuator towards the distal end of the housing to close both the distal and proximal valves. Further, the proximal valve comprises a proximal seal disposed at the proximal end of the housing, the seal being formed as a septum. In another aspect, the septum is connected to the resilient member.

In other aspects, the actuator comprises a distal end and a proximal end, the proximal end comprising a piercing element located so as to pierce the proximal valve upon movement of the actuator in the proximal direction. Further, the piercing element includes a lumen through which fluid may flow. In another aspect, the piercing element includes a longitudinal slot through which fluid may flow. The distal end of the actuator comprises a valve stem within which a fluid flow lumen is disposed. The actuator further comprises a tip seal located at a distal end of the valve stem, which, when the actuator is in a distal position within the housing, closes the distal valve to prevent the flow of fluid through the distal valve. The actuator further comprises an orifice at a distal end of the valve stem, the orifice disposed in fluid communication with a lumen of the valve stem to form a fluid flow channel through the actuator. The orifice is formed through a longitudinal wall surrounding the valve stem lumen.

In yet further detailed aspects of the invention, the connector further comprising a hollow resilient member contained within the housing and positioned to bias the actuator towards the distal end of the housing to close both the distal and proximal valves, a hollow portion of the resilient member being disposed in fluid communication with the lumen of the valve stem to provide a flow channel between the distal valve and the proximal valve. The piercing member is disposed on the actuator so that as the actuator moves in the proximal direction, the distal valve opens before the proximal valve opens. In another aspect, the piercing member is disposed on the actuator so that as the actuator moves in the distal direction, the proximal valve closes before the distal valve closes.

In still further detailed aspects, the actuator comprises a valve stem located within the tubular male portion, the valve stem having a tip seal forming a part of the first valve wherein the tip seal is located at a distal end of the valve stem which, when the actuator is in the distal position, closes the first valve to prevent the flow of fluid through the first valve, a lumen formed in the valve stem through which fluid may flow, an orifice formed at the distal end of the valve stem through which fluid may flow into and out of the lumen, and a sliding seal located between an external surface of the valve stem and engaging an inner surface of the male portion proximal to the orifice so as to provide a fluid seal between the male Luer portion and the valve stem.

In another aspect, the actuator is formed so that as it moves in the distal direction, it closes the distal valve and proximal valve sequentially to result in a partial vacuum being formed at the male Luer portion opening to draw fluid into the male Luer portion. Further, a flow channel is disposed through the tubular male portion, the distal valve, the actuator, and the proximal valve.

In additional aspects of the invention, a self-sealing male Luer connector is provided for connection with a female Luer connector, the male Luer connector comprising a rigid housing having a distal end and a proximal end, the housing comprising at the distal end a rigid tubular male Luer portion having a shape configured for engagement with a female Luer connector, a distal valve located at the distal end of the housing, the distal valve comprising an internal valve seat disposed in the tubular male Luer portion. a proximal valve located at the proximal end of the housing, an actuator movably disposed within the housing for movement toward the proximal end of the housing to open both the distal and proximal valves, the actuator comprising a distal end having a valve stem within which a fluid flow lumen is disposed, and a tip seal located at a distal end of the valve stem, which, when the actuator is in a distal position, closes the first valve to prevent the flow of fluid through the first valve, and wherein the actuator further comprises an actuator arm disposed adjacent and outside the tubular male portion wherein movement of the actuator arm from a first position to a second position in the housing will cause the actuator to move towards the proximal end of the housing and open both the distal and proximal valves; and a resilient member contained within the housing and positioned to bias the actuator towards the distal end of the housing to close both the distal and proximal valves, whereby the actuator arm is configured to move from the first position to the second position when a female connector is engaged with the Luer male portion.

Also in accordance with method aspects of the invention, there is provided a method of engaging a male connector with a female connector, comprising inserting a tubular male portion of the male connector into the female connector, the male connector having a distal end at which the male portion is located and a proximal end, moving an actuator positioned within the tubular male portion in a proximal direction as the male portion and female connector are engaged, opening a distal valve located at the distal end of the male connector and a proximal valve located at the proximal end of the male connector with the actuator as the actuator is being moved in the proximal direction, disengaging the tubular male portion of the male connector from the female connector, moving the actuator in a distal direction as the male portion and female connector are disengaged, and closing the proximal and distal valves as the actuator is being moved in the proximal direction.

In further detailed method aspects, the method further comprises the step of piercing a proximal seal that forms the proximal valve with a piercing element that forms a part of the actuator. The step of opening the distal and proximal valves comprises opening first the proximal valve and then opening the distal valve. The step of closing the proximal and distal valves comprises closing first the proximal valve and then closing the distal valve.

In yet other detailed method aspects of the invention, the step of closing the proximal and distal valves comprises closing first the proximal valve, producing within the housing a partial vacuum at the distal end of the housing, drawing fluid residing on an outer distal surface of the housing into the housing with the partial vacuum, and then closing the distal valve. The step of producing the partial vacuum comprises allowing an internal resilient member to bias the actuator toward the distal end of the housing thereby increasing the volume inside the resilient member as such movement of the actuator toward the distal end occurs thereby creating the partial vacuum within the housing to draw fluid into the housing.

These and other advantages of the invention will become apparent from the following more detailed description when taken in conjunction with the accompanying drawings of illustrative embodiments.

BRIEF DESCRIPTION OF THE DRAWINGS

FIG. 1 depicts a perspective view of a self-sealing male Luer connector in accordance with aspects of the invention;

FIG. 2 depicts a side elevation view of the male Luer connector shown in FIG. 1;

FIG. 8 depicts a side-elevation view of one embodiment of an actuator used in a self-sealing male connector in accordance with aspects of the invention, wherein the actuator is used to open internal valves of the male connector;

FIG. 9 depicts a side-elevation view of the actuator shown in FIG. 8 rotated 90 degrees;

FIG. 10 depicts a cross-sectional view of the actuator shown in FIGS. 8 and 9; and FIG. 11 depicts a top planar view of the actuator shown in FIG. 8 in which the actuator has four actuator arms.

DETAILED DESCRIPTION OF THE PREFERRED EMBODIMENTS

Figure 3:
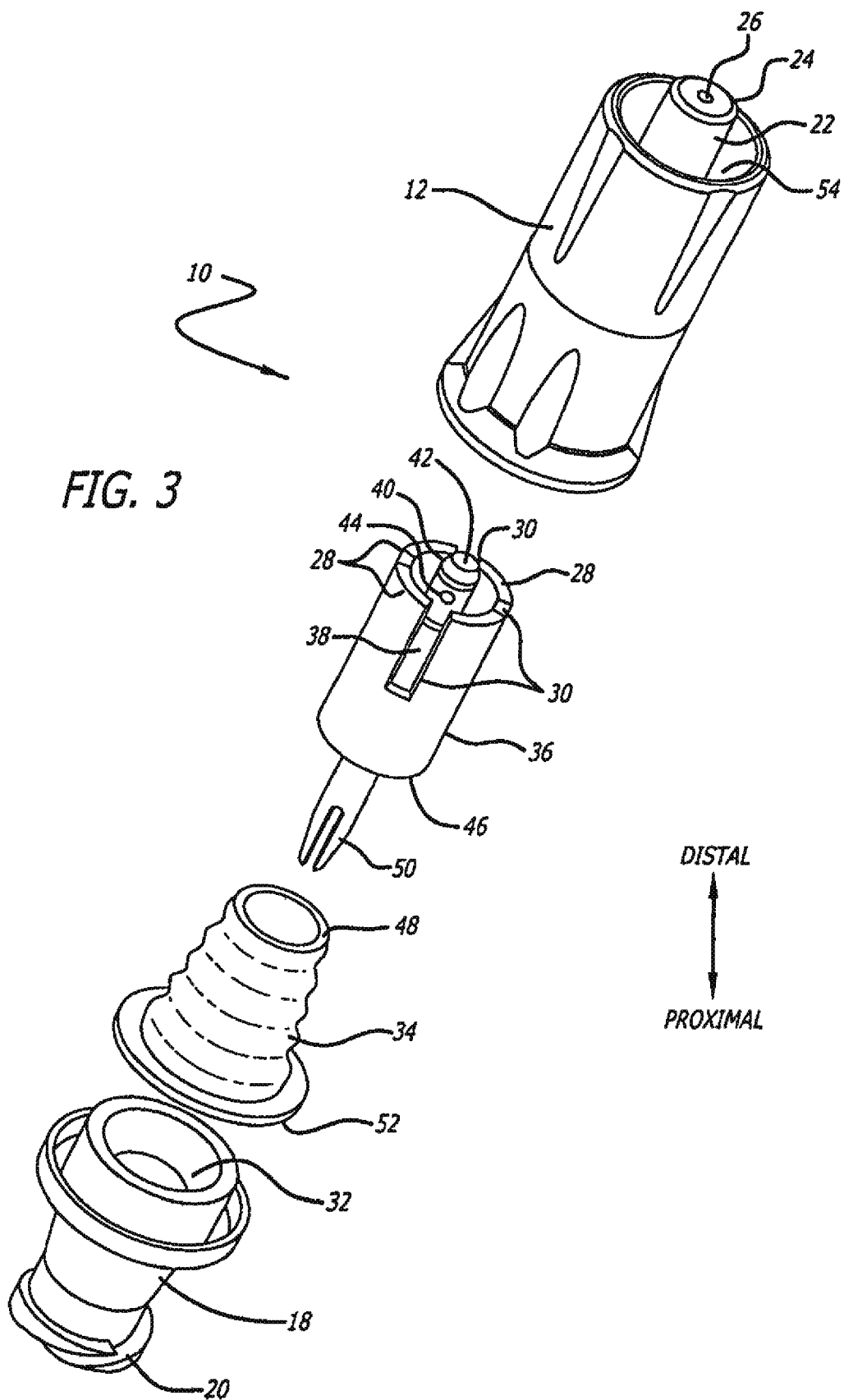
FIG. 3 is an exploded view of the components that form the self-sealing male Luer connector of FIGS. 1 and 2.

Referring now to the drawings in more detail for purposes of illustration, wherein like reference numerals designate corresponding or like elements among the several views, there is shown in FIGS. 1 and 2, a self-sealing male Luer connector 10 in accordance with one embodiment of the present invention. The self-sealing male Luer connector is intended to engage a standard female Luer connector. The female Luer connector is not limited to a particular type.

In this embodiment, the male Luer connector 10 includes a housing 12 having a proximal end 14 and a distal end 16, at which a female connector may be engaged. The housing may have a generally cylindrical shape as shown and terminate at the proximal end in a connector of some type, or other mounting configuration for connection to another fluid flow device, such as tubing. As shown in FIGS. 1 and 2, in this case the proximal end 14 of the housing 12 has mounted to it a female adapter 18 for connection with various male devices or containers. External threads 20 are shown positioned about the female adapter for engagement with threads located on a complementary male connector. The female adapter may be designed to have a standard ANSI-HIMA female Luer taper with standard sizes of opening, length, and thread size, although in other embodiments, the female adapter may take other shapes and sizes.

At the distal end 16, the self-sealing male Luer connector device 10 also includes a male Luer portion 22 that projects in the distal direction from within the housing 12. The male Luer portion may also be of the standard ANSI-HIMA male Luer taper with standard outer diameter and length, although in other embodiments, the male Luer portion 22 may take other shapes and sizes. The male Luer portion has a distal end 24 at which is formed a distal fluid flow opening 26 through which fluid may flow into and out of the self-sealing male Luer connector device 10. Also see in FIG. 1 are two actuator arms 28 that function to open an internal valve or valves upon engagement with a female connector. Although two actuator arms are shown, in other embodiments, fewer or more actuator arms may be used. The actuator arms in FIG. 1 are evenly-spaced about the male Luer portion with spaces or gaps 30 between them.

Now referring to FIG. 3, an exploded view of the self-sealing male Luer device 10 of FIGS. 1 and 2 is shown. The female adapter 18 has been separated from the housing 12 and a flow channel 32 formed through it can be seen. The female adapter includes mounting features to accept the housing and an internal resilient biasing device 34, but such features are within the skill of those in the art and no further description will be provided at this point. An actuator 36 includes the actuator arms 28 shown in FIG. 1, although four arms are shown in this figure. The actuator includes a valve stem 38 that interacts with a valve seat in the housing, which will be described in further detail below and shown in other figures. The valve stem has a distal end 40 at which is mounted a tip seal 42 for closing the valve created by the valve stem and a valve seat, as will be described later. Also, the valve stem includes a fluid flow orifice 44 into which and out of which fluid may flow through the hollow valve stem. The actuator includes a base 46 from which the actuator arms extend in the distal direction, and although not visible in this figure, a mounting groove for accepting and containing the distal end 48 of the resilient biasing device. Lastly, the actuator includes a proximally extending piercing element 50 which is useful to open a flow passage through a septum forming a part of the resilient biasing device at its proximal end 52, although the septum cannot be seen in this figure.

The housing 12 is also shown with the male Luer portion 22 shown protruding in the distal direction from the cylindrical housing. The distal end 24 of the male Luer portion includes the fluid opening 26 through which fluid may flow into and out of the self-sealing male Luer connector 10. The actuator arms 28 from the actuator 36 will be disposed in the space 54 between the male Luer portion and the cylindrical housing portion, as will the female Luer connector when mounted to the self-sealing male Luer connector 10.

Figure 4:
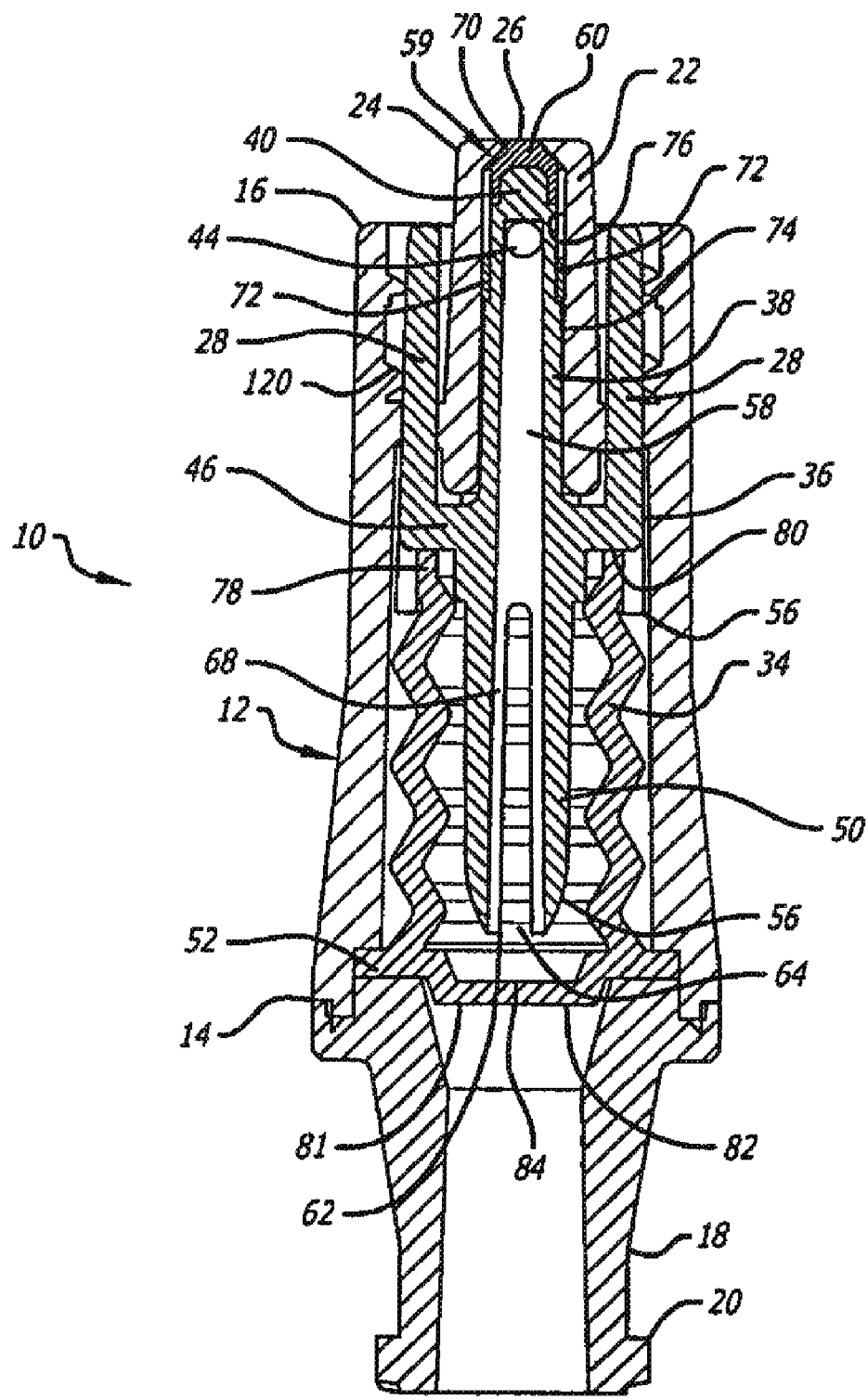
FIG. 4 depicts a cross-sectional view of the self-sealing male Luer connector taken along line A-A of FIG. 2 in an unactuated state.

Referring now to FIG. 4, the components shown in FIG. 3 have been assembled into the self-sealing Luer connector 10 of FIGS. 1 and 2 and a cross-section view of the assembled connector device taken along lines 4-4 of FIG. 2 is shown. The actuator 36 is positioned within the housing and includes the base section 46 from which the actuator arms 28 extend in the distal direction. The actuator includes a distal end 40 and a proximal end 56, and a fluid flow channel 58 located longitudinally through the actuator. The valve stem 38 extends in the distal direction from the base 46 and the flow channel is formed through the valve stem. At the distal end of the male Luer portion 22, a distal valve 59 is formed. In this embodiment, the valve tip seal 42 mounted at the distal end 40 of the valve stem forms a part of the distal valve. At the distal end is also formed an orifice 44 that interconnects with the internal longitudinal fluid flow channel 58. In the present embodiment, the aperture comprises a through hole that extends completely through the distal end of the actuator tube radially such that there are two holes formed through opposite sides of the cylindrical wall of the valve stem, although in another embodiment, it is possible that only one hole is formed through the wall of the valve stem. The size and shape of the orifice may be varied to optimize fluid flow rates and reduce turbulence of flow through the male device.

Figure 6:
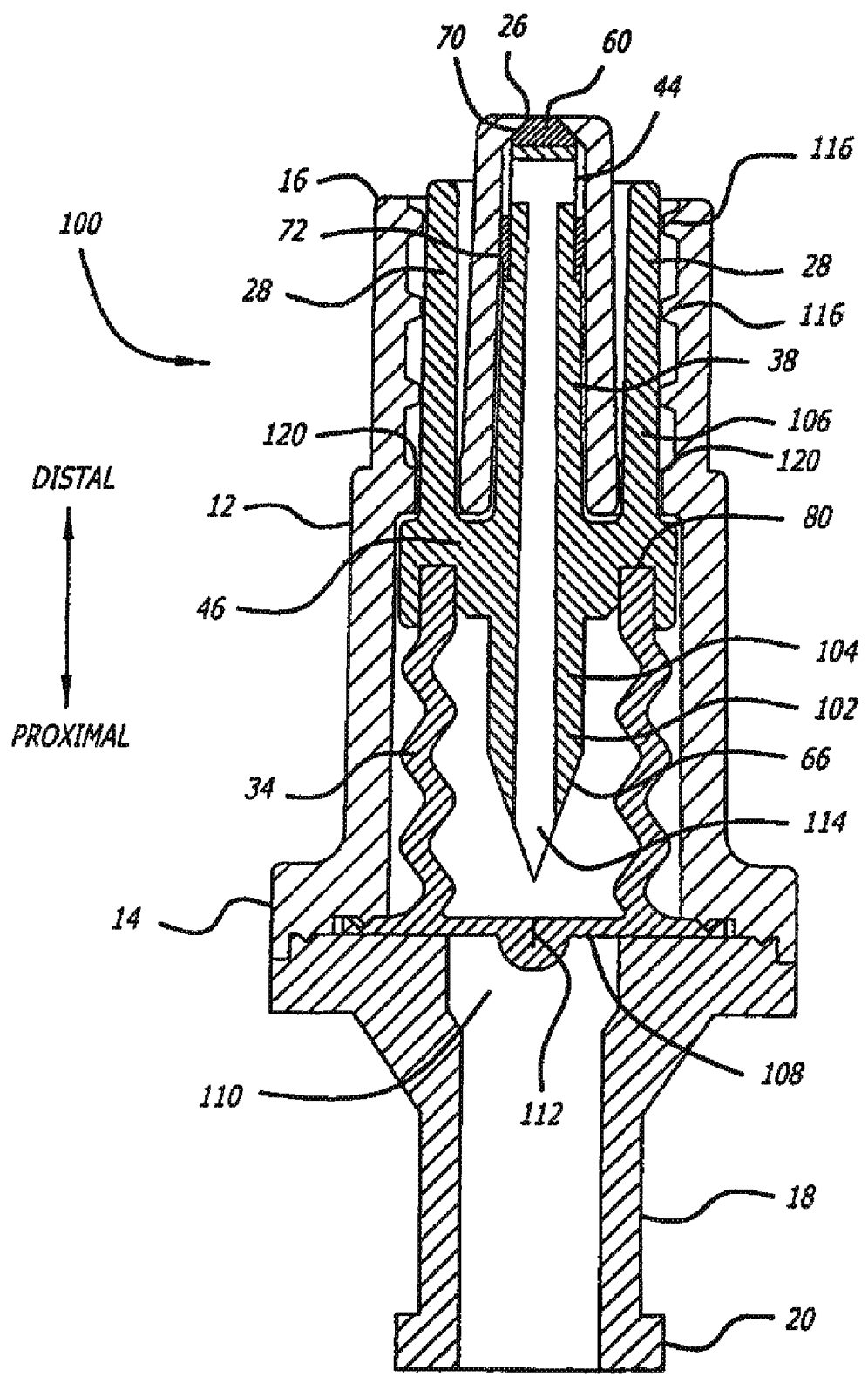
FIG. 6 depicts a cross-sectional view of another embodiment of a self-sealing male Luer connector in accordance with aspects of the invention in an un-actuated state wherein the male connector includes a piercing element as part of an actuator.
Figure 7:
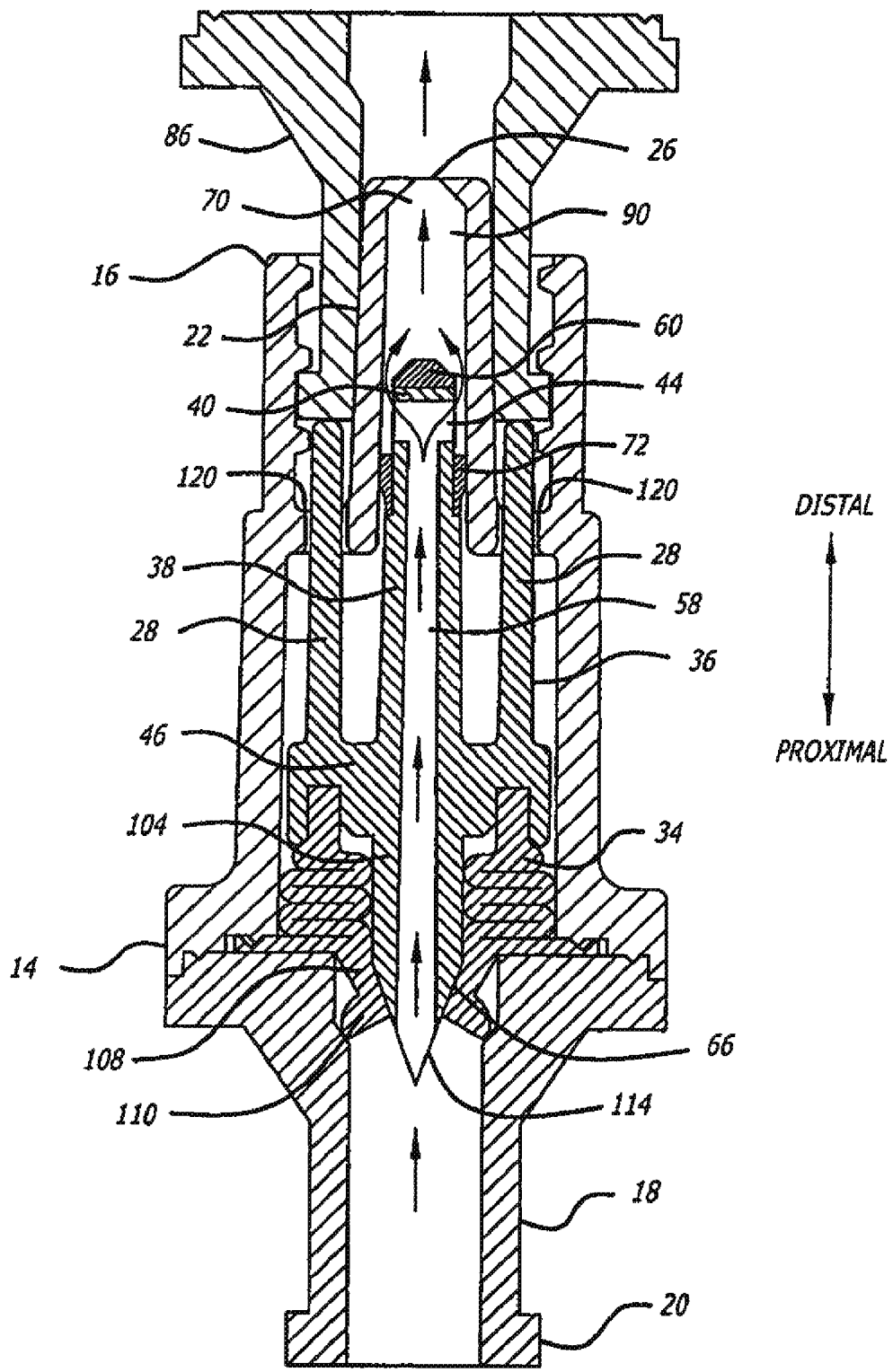
FIG. 7 depicts a cross-sectional view of the self-sealing male Luer connector of FIG. 6 engaged with a female connector and thereby in the actuated state.

The proximal end 56 of the actuator includes a piercing element 50. In the embodiment shown in FIG. 4, the piercing element includes a blunt end 62 that may be tapered or rounded. An aperture 64 is disposed at the blunt end of the piercing element so that fluid may enter the longitudinal flow channel 58. The piercing element may also include a spike 66 as shown in FIGS. 6 and 7. In this embodiment, there is at least one longitudinal slot 68 formed in the wall of the actuator extending to its proximal end. The slot helps to ensure that all fluids and gases contained within the resilient member can easily flow into and out of the actuator both during use and when disconnecting the mating component. Although it cannot be seen in this view because it is a cross-section, there are two longitudinal slots located opposite each other in the wall of the actuator. In other embodiments the actuator may not include a slot.

The valve stem 38 of the actuator 36 includes the tip seal 42 at its distal end for sealing engagement with a valve seat 70 formed internally at the distal end 24 of the male Luer portion 22. The valve seat 70, tip seal 42, and valve stem 38 form the distal valve 59 in this embodiment. In one embodiment there is also a sliding seal 72 disposed at the distal end 40 of the actuator 36 as well. The sliding seal is disposed proximally from the orifice 44 in the valve stem 38, so that the aperture is between the tip seal 42 and the sliding seal 72. The sliding seal prevents fluid from escaping between the outer wall 74 of the actuator and the inner wall 76 of the male Luer portion 22. Both the tip seal and the sliding seal may be joined together, and in other embodiments the seals may be separate. The combined seals can be created by over molding a soft, thermoplastic elastomer onto the hard plastic of the valve stem of the actuator, allowing the seals and actuator to be molded together. This reduces the number of required components and eliminates the need to join the tip seal and the sliding seal to the actuator as a separate manufacturing step. This "joined" design is presented in FIG. 8. The tip seal can be a poppet valve and the sliding seal can be a dynamic O-ring seal. It has also been contemplated that the tip seal and the sliding seal could be separately molded or otherwise formed from a soft, compliant material, and press fit or joined to the first end of the actuator.

Referring again to FIG. 4, the resilient member 34 is contained within the housing 12 and includes a distal end 78 that abuts the actuator 36 at the proximal end 56 of the actuator. In one embodiment the resilient member fits within a groove 80 formed in the base 46 of the actuator. The proximal end 52 of the resilient member is secured to the proximal end 14 of the housing by being clamped between the housing and the adapter 18. In this embodiment the resilient member is a cylindrical flexible spring formed of silicone that also acts as a seal to contain fluid within the housing. The resilient member or spring is positioned within the housing in a slightly compressed state to continually bias the actuator toward the distal end 16 of the housing. This biasing force creates a tight seal between the tip seal 42 and the valve seat 70. However, in another embodiment, it may be possible that the resilient member is installed within the housing such that it is uncompressed when the self-sealing male Luer connector 10 is in its non-actuated state.

While the resilient member 34 or silicone spring is shown as an accordion shaped member, it could be made in several other configurations, including an elongated O-ring shape. Further, the shape and the thickness of the resilient member can be changed to increase or decrease both the spring or biasing force that the resilient member generates, as well as the internal volume change it generates between a compressed state (FIG. 5) and an extended state (FIG. 4).

In the embodiment shown in FIG. 4, the self-sealing male Luer connector 10 further includes a proximal valve 81 located at the proximal end of the housing 12. A proximal seal 82 in the form of a septum in this embodiment is disposed at the proximal end 14 of the housing 12 to seal against fluid or air pressures applied to the self-sealing male Luer connector 10 from the proximal end of the housing. A slit 84 is created in the proximal seal in the embodiment shown, although in other embodiments, no slit may be pre-formed in the proximal seal or only a partial slit may be formed. The proximal seal may be a check-valve seal as shown in FIG. 4 or in some embodiments may be a duck-bill check valve such as that shown in FIGS. 6 and 7. In one embodiment the proximal seal is formed as part of the resilient member 34, or they are otherwise joined together. The proximal seal and the resilient member may be created by molding a soft, thermoplastic elastomer to form one component without having to mechanically join the resilient member to the proximal seal. The shape of the proximal seal, its thickness, and the slit can be changed to optimize seal pressure and the ease with which the proximal seal opens when contacted by the piercing element 50 of the actuator.

It can therefore be seen from FIG. 4 that a flow channel exists completely through the male connector 10. At the distal end, the flow channel begins at the distal tip 24 of the male Luer portion through the opening 26, proceeds through the distal valve 59, through the orifice 44 of the valve stem 38, through the lumen 58 of the valve stem 38, through the proximal valve 81, through the aperture 64 of the piercing element 50, and through the flow channel 32 of the female adapter 18.

Figure 5:
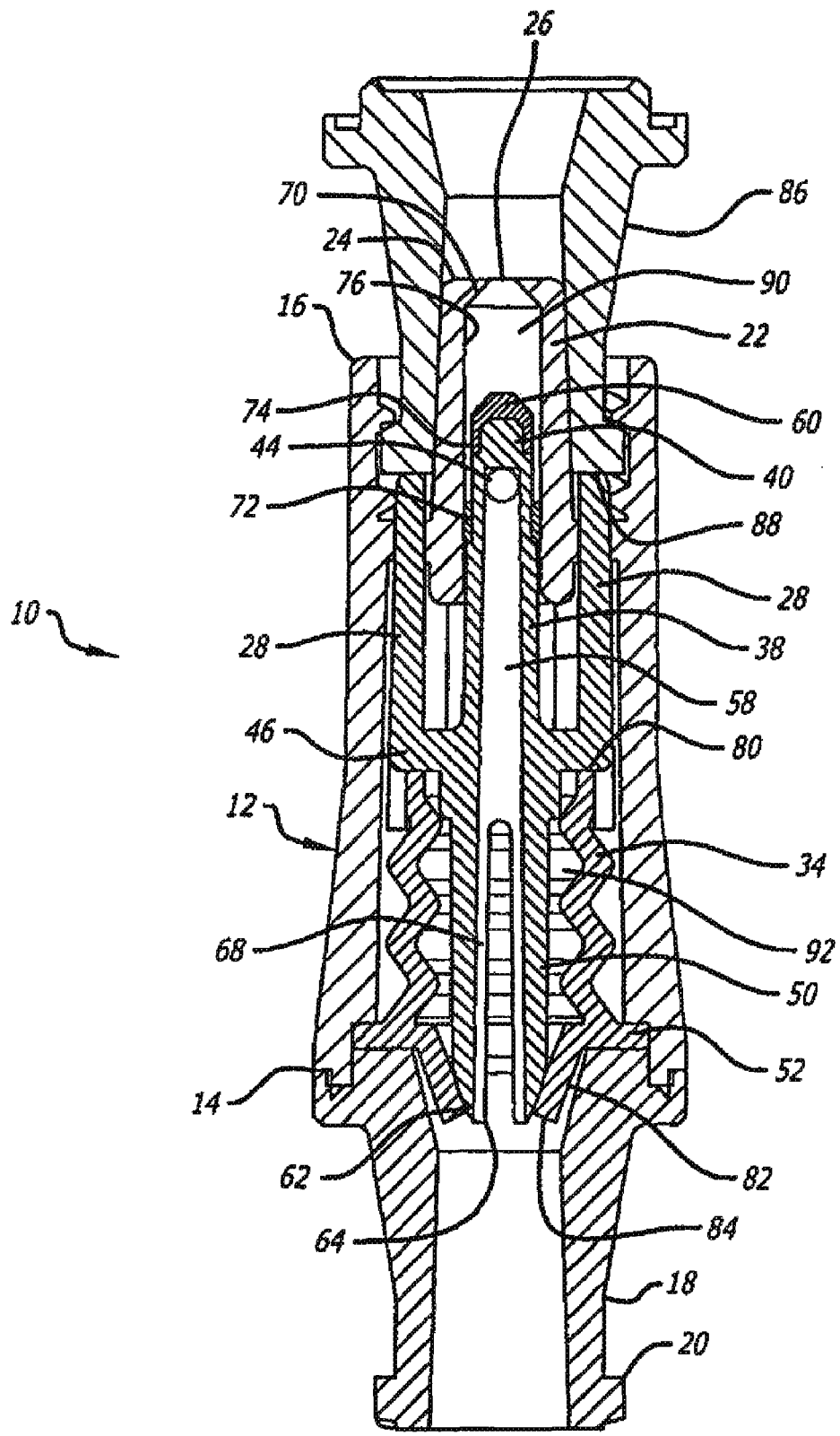
FIG. 5 depicts a cross-sectional view of the self-sealing male Luer connector taken along line A-A of FIG. 2 engaged with a female Luer connector thus placing the male connector in an actuated state.

Referring now to FIG. 5, the self-sealing male Luer connector 10 is shown engaged with a standard female Luer connector 86, such that the male Luer device is in an actuated state. As the female connector is threaded onto the male Luer connector, the front surface 88 of the female connector comes into contact with the actuator arms 28 of the actuator 36 and moves the actuator in the proximal direction. This movement also moves the tip seal 42 of the valve stem 38 of the actuator in the proximal direction away from the valve seat 70, thereby opening the distal orifice 26 for the flow of fluid. The movement of the actuator in the proximal direction collapses the resilient member 34 and forces the blunt end 62 of the piercing element 50 through the slit 84 of the proximal seal 82 thereby opening this seal to allow the flow of fluid through the proximal end of the housing. In this fully actuated state, the tip seal and the proximal seal are open, allowing bi-directional fluid flow through the self-sealing male Luer connector. As fluid flows through the male connector, the sliding seal 72 prevents fluid from escaping between the outer wall 74 of the actuator 36 and the inner wall 76 of the male Luer portion 22. In one embodiment, the dimensions of the actuator are such that the tip seal on the valve stem is removed from the valve seat at the distal end 40 of the male Luer portion before the piercing element passes through and opens the proximal seal.

When fluid is transferred through the self-sealing male Luer connector 10 and into the female Luer connector 86, the flow path through the male Luer device includes flowing into the aperture 64 on the piercing element 58 of the actuator 36. The fluid then flows through the lumen 58 of the actuator and exits the actuator via the distal orifice 44 located near the distal end 40 of the actuator. Fluid continues to flow from the orifice of the valve stem to the lumen 90 formed by the male Luer portion and out through the distal opening 26 of the male Luer portion and into the female Luer connector. This flow path is reversed when fluid is transferred from the female Luer connector to the male Luer device.

As the female Luer connector 86 is removed from the self-sealing male Luer connector 10, the actions described above occur in reverse as the actuator 36 is forced to move in the distal direction toward the distal end 16 of the housing 12 by the resilient member 34. The dimensions of the actuator are such that the slit 84 in the proximal seal 82 closes before the tip seal 42 is securely pressed in a sealing relationship against the valve seat 70. As the resilient member or silicone spring extends itself from a compressed position to an extended position, the volume of space 92 inside the resilient member increases, and because the proximal seal closes before the tip seal closes at the distal end, a partial vacuum is created in the flow path 58 that will be directed toward the unsealed distal end 24 of the male Luer portion 22. Any fluid remaining near the distal opening 26 of the male Luer portion will be drawn into the male Luer portion by this partial vacuum before the distal opening is finally sealed by the tip seal 42.

Referring to FIGS. 6 and 7, another embodiment of the self-sealing male Luer connector 10 in accordance with aspects of the invention is shown. FIG. 6 shows the self-sealing male Luer connector in the non-actuated state, and the male connector 10 shown is very similar to the device of FIG. 4. In this embodiment, however, the piercing element 102 includes a spike 66 at the proximal end 104 of the actuator 106. Also, this embodiment includes a proximal seal 108 that includes a duck-bill 110 for sealing against greater reverse pressure. Another difference between this embodiment and the embodiment shown in FIG. 4 is that no slit is formed in the proximal seal, or only a partial slit; that is, a slit formed through a part of the duck bill structure instead of all the way through. The latter construction is shown in FIG. 6. Aperture 114 in the spike forms a part of the flow lumen 58 through the actuator of the self-sealing male Luer connector. Other than the changes to the actuator and the proximal seal, the self-sealing male Luer connector of FIGS. 6 and 7 is the same as the male connector of FIGS. 1 through 5.

It can be noted in FIGS. 4, 5, 6, and 7, that the distal end 16 of the housing contains internal threads 116. These threads are used to engage the external threads of a female connector, as shown in FIGS. 5 and 7 so that the two connectors are more securely held together. Although the housing 12 and internal threads 116 are integral, other embodiments may be formed. For example, the housing may be formed so as to have a freely rotating distal section within which the threads are formed. This then effectively results in a threaded collar and with such a design, only the collar need be rotated to lock the female connector to the male connector. Otherwise, either the female or male connector must be rotated in its entirety in relation to the other connector to achieve threaded engagement.

FIG. 7 shows the self-sealing male Luer connector 10 engaged with the female Luer connector 86 and the arrows show the fluid path through the male connector and the female connector. In this actuated state, fluid is forced to flow through the aperture 114 of the spike 66 and through the lumen 58 of actuator 36. The fluid then flows out of the orifice 44 on both sides of the actuator, forming a T-shaped junction in the flow path 58. Once out of the actuator, the fluid flows through the lumen 90 of the male Luer portion 22 and then out through the distal opening 26 of the male Luer portion and into the female Luer connector. It is possible to modify the shape of the T-shaped junction in the flow path to optimize fluid flow rates and to reduce turbulence of flow by changing the size, shape, and position of the through hole.

FIGS. 8-11 show the actuator 106 of the self-sealing male Luer connector 10 of FIGS. 6 and 7 in greater detail. Other than the proximal end 104 of the actuator 106, the actuator shown is also very similar to the embodiment of the actuator shown in FIGS. 3 and 4 that includes a blunt end and a slot. FIG. 8 is a side elevation view of the actuator including the actuator arms 28 separated by gaps 118. As shown in FIG. 11, which is a top planar view of the actuator, this particular embodiment includes four evenly-spaced actuator arms 28 that extend from the base section 46. It can be noted from a study of FIGS. 4 through 7 that the male Luer portion 22 is formed as a part of the housing. The male Luer portion is coaxially located partially within the housing by means of struts 120 between it and the inside surface of the housing. The number of struts matches the number of gaps between the actuator arms. During assembly of the actuator with the housing, the actuator is rotated so that its arms are positioned between the struts that suspend the male Luer portion within the housing.

In the embodiment shown in FIG. 9, the orifice 44 is best shown disposed at the distal end of the actuator. The orifice extends through the first end of the valve stem 38 such that there are two holes formed through the cylindrical wall of the valve stem on opposite sides as shown in FIG. 10, although it is possible that only one aperture is formed through the wall of the actuator. Also the aperture 114 of the spike 66 is shown in FIGS. 8, 9, and 10.

It should be understood that the use of the terms "distal" and "proximal" is meant as a reference to direction and not as limiting on the invention. As an example of the materials selected for the embodiments shown, the housing 12 was formed of a rigid polycarbonate, the actuator 36 was formed of a rigid polypropylene, the resilient member 34 was formed of a resilient material such as silicone, and the female adapter 18 was formed of a rigid polycarbonate. The tip seal 42 and the sliding seal 72 were formed of a resilient material known as thermoplastic elastomer. Because the proximal seal 82 was formed as part of the resilient member, it too was formed of the resilient silicone. This is beneficial in that it is desirable for the proximal seal to return to its original position and sealed configuration upon withdrawal of the piercing element 50. The self-sealing male Luer connector 10 may then be accessed multiple times.

Although exemplary embodiments of the invention have been described above by way of example only, it will be understood by those skilled in the field that modifications may be made to the disclosed embodiments without departing from the scope of the invention, which is defined by the appended claims.

What is claimed is:

1. A self-sealing male connector for connection with a female connector, the male connector comprising:
   a rigid housing having a distal end and a proximal end, the housing comprising at the distal end a rigid tubular male portion having a shape configured for engagement with a female connector;
   a distal valve located at the distal end of the housing, the distal valve comprising an internal valve seat disposed in the tubular male portion;
   a proximal valve located at the proximal end of the housing;
   an actuator disposed within the housing and configured to be movable towards the proximal end of the housing to cause opening of first the distal and then the proximal valves, the actuator comprising an actuator arm disposed adjacent and outside the tubular male portion wherein movement of the actuator arm from a first position to a second position causes the actuator to move towards the proximal end of the housing thereby opening first the distal and then the proximal valves, wherein the actuator comprises a distal end and a proximal end, the proximal end comprising a piercing element located so as to pierce the proximal valve upon movement of the actuator in the proximal direction; and
   a hollow resilient member contained within the housing and configured to bias the actuator towards the distal end of the housing, the hollow resilient member coupled to the housing and to the actuator to form an internal volume that is fluidically coupled to the distal valve, the hollow resilient member configured such that the internal volume has a first volume when the actuator arm is in the first position and a second volume when the actuator arm is in the second position, the second volume being smaller than the first volume;

whereby the actuator arm is configured to move from the first position to the second position when a female connector is engaged with the tubular male portion, and from the second position to the first position when the female connector is removed from the tubular male portion, and wherein as the actuator moves in the distal direction, the proximal valve closes before the distal valve closes.

2. The connector of claim 1 wherein the distal end of the actuator comprises a valve stem within which a fluid flow lumen is disposed.

3. The connector of claim 2 wherein the actuator further comprises an orifice at a distal end of the valve stem, the orifice disposed in fluid communication with a lumen of the valve stem to form a fluid flow channel through the actuator.

4. The connector of claim 3 wherein the orifice is formed through a longitudinal wall surrounding the valve stem lumen.

5. The connector of claim 2 wherein the actuator further comprises a tip seal located at a distal end of the valve stem, which, when the actuator is in a distal position within the housing, closes the distal valve to prevent the flow of fluid through the distal valve.

6. The connector of claim 1 wherein the proximal valve comprises a proximal seal disposed at the proximal end of the housing, the seal being formed as a septum.

7. The connector of claim 6 wherein the septum is connected to the resilient member.

8. The connector of claim 1 wherein the piercing element includes a lumen through which fluid may flow.

9. The connector of claim 8 wherein the piercing element includes a longitudinal slot through which fluid may flow.

10. The connector of claim 1 wherein the actuator comprises:
a valve stem located within the tubular male portion, the valve stem having a tip seal forming a part of the first valve wherein the tip seal is located at a distal end of the valve stem which, when the actuator is in the distal position, closes the first valve to prevent the flow of fluid through the first valve;
a lumen formed in the valve stem through which fluid may flow;
an orifice formed at the distal end of the valve stem through which fluid may flow into and out of the lumen; and
a sliding seal located between an external surface of the valve stem and engaging an inner surface of the male portion proximal to the orifice so as to provide a fluid seal between the male Luer portion and the valve stem.

11. The connector of claim 1 comprising a flow channel disposed through the tubular male portion, the distal valve, the actuator, and the proximal valve.

12. A self-sealing male Luer connector for connection with a female Luer connector, the male Luer connector comprising:

a rigid housing having a distal end and a proximal end, the housing comprising at the distal end a rigid tubular male Luer portion having a shape configured for engagement with a female Luer connector;
a distal valve located at the distal end of the housing, the distal valve comprising an internal valve seat disposed in the tubular male Luer portion;
a proximal valve located at the proximal end of the housing;
an actuator movably disposed within the housing for movement toward the proximal end of the housing to open first the distal and then the proximal valves, the actuator comprising a distal end having a valve stem within which a fluid flow lumen is disposed, and a tip seal located at a distal end of the valve stem, which, when the actuator is in a distal position, closes the first valve to prevent the flow of fluid through the first valve, and wherein the actuator further comprises an actuator arm disposed adjacent and outside the tubular male portion wherein movement of the actuator arm from a first position to a second position in the housing will cause the actuator to move towards the proximal end of the housing and open first the distal and then the proximal valves, wherein the actuator comprises a distal end and a proximal end, the proximal end comprising a piercing element located so as to pierce the proximal valve upon movement of the actuator in the proximal direction; and
a hollow resilient member contained within the housing and configured to bias the actuator towards the distal end of the housing, the hollow resilient member coupled to the housing and to the actuator to form an internal volume that is fluidically coupled to the distal valve, the hollow resilient member configured such that the internal volume has a first volume when the actuator arm is in the first position and a second volume when the actuator arm is in the second position, the second volume being smaller than the first volume;
whereby the actuator arm is configured to move from the first position to the second position when a female connector is engaged with the Luer male portion, and from the second position to the first position when the female connector is removed from the Luer male portion, and wherein as the actuator moves in the distal direction, the proximal valve closes before the distal valve closes.

13. The connector of claim 12 wherein the actuator further comprises an orifice at the distal end of the valve stem, the orifice being formed through a longitudinal wall surrounding the valve stem lumen to thereby be in fluid communication with the lumen of the valve stem to form a fluid flow channel through the actuator.

14. The connector of claim 13 further comprising a sliding seal located between an external surface of the valve stem and an inner surface of the male Luer portion at a location proximal to the orifice so as to provide a fluid seal between the male Luer portion and the valve stem.

* * * * *